United States Patent [19]
Mehdizadeh

[11] Patent Number: 5,961,522
[45] Date of Patent: Oct. 5, 1999

[54] LAMINECTOMY CHISEL AND GUIDE APPARATUS

[76] Inventor: Hamid M. Mehdizadeh, 14928 Diduca Way, Los Gatos, Calif. 95032

[21] Appl. No.: 08/966,440

[22] Filed: Nov. 10, 1997

[51] Int. Cl.⁶ ................................................. A61B 17/56
[52] U.S. Cl. ............................................... 606/79; 606/84
[58] Field of Search .................. 606/79, 80, 81, 606/82, 83, 84, 85, 86, 96, 87

[56] References Cited

U.S. PATENT DOCUMENTS

| | | | |
|---|---|---|---|
| 1,934,962 | 11/1933 | Barry | 606/84 |
| 2,487,221 | 11/1949 | Cooke | 606/84 |
| 4,349,058 | 9/1982 | Comparetto | 606/84 |
| 4,686,978 | 8/1987 | Wadsworth | 606/84 |
| 4,782,833 | 11/1988 | Einhorn et al. | 606/80 |
| 4,881,534 | 11/1989 | Uhl et al. | 606/84 |
| 5,133,719 | 7/1992 | Winston | 606/79 |
| 5,250,061 | 10/1993 | Michelson | 606/160 |

*Primary Examiner*—Michael Buiz
*Assistant Examiner*—Vy Bui
*Attorney, Agent, or Firm*—Henry M. Stanley

[57] ABSTRACT

A set of bone chisels is disclosed for use in laminectomy procedures wherein portions of the lamina, facet, and pedicle have to be removed for successful performance of the surgery. The chisels are shaped for use in conjunction with a tubular nerve root retractor which also spreads or spaces vertebral bodies in accordance with some surgical procedures.

16 Claims, 2 Drawing Sheets

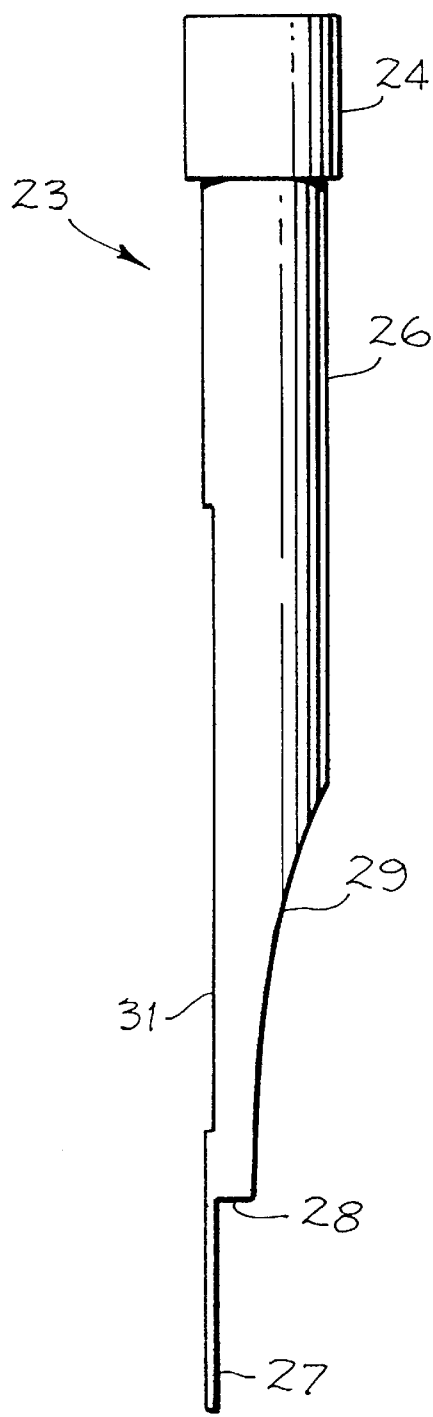
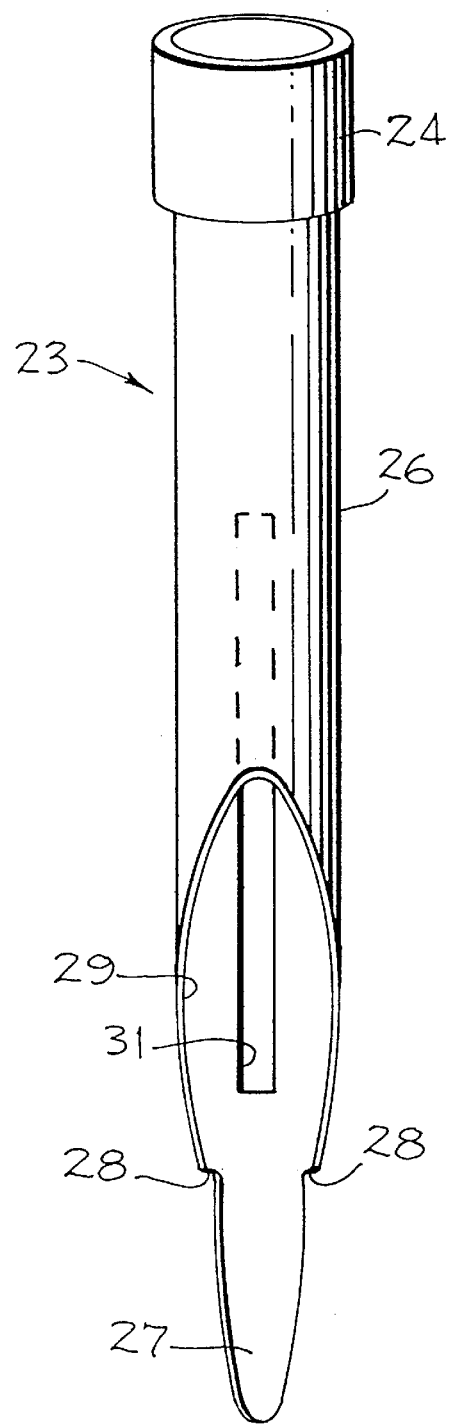

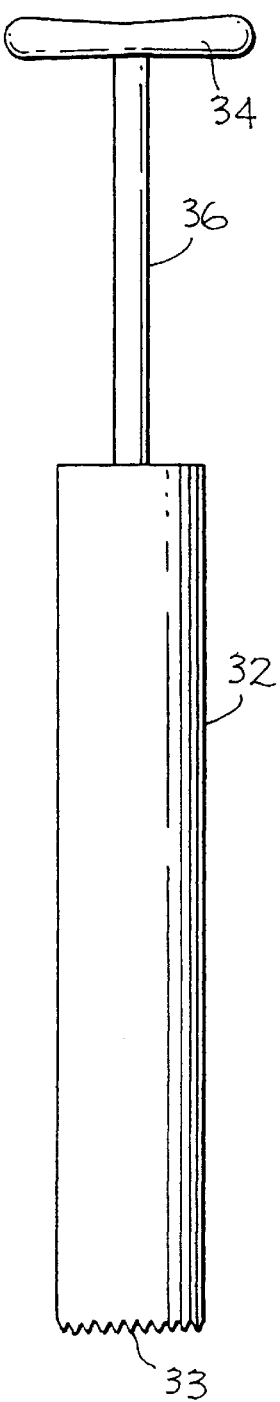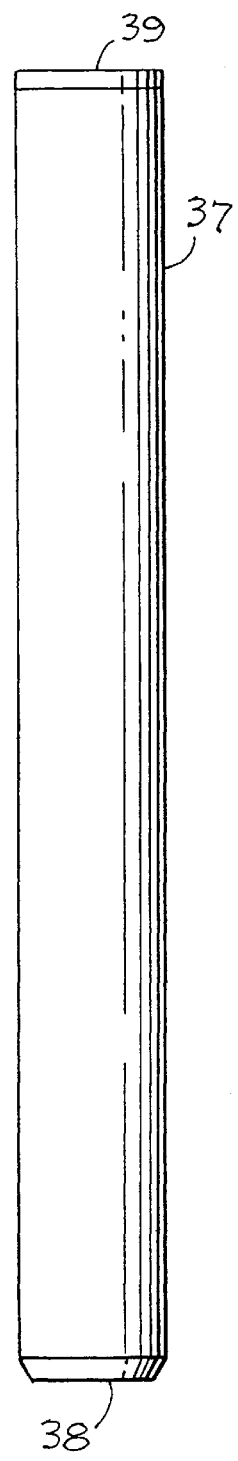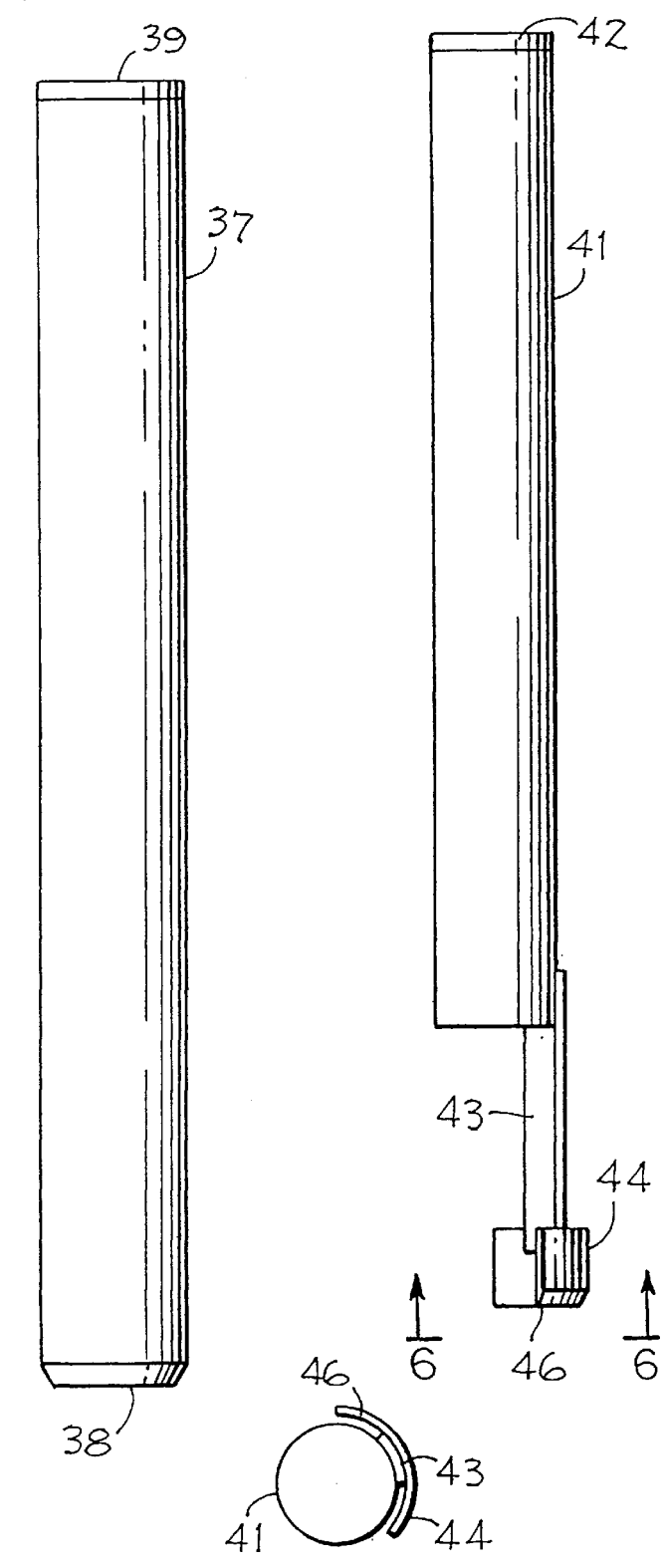

LAMINECTOMY CHISEL AND GUIDE APPARATUS

SUMMARY OF THE INVENTION

A bone chisel and guide therefor is disclosed for use in laminectomy procedures, wherein the combination includes a chisel used in conjunction with a guiding nerve root retractor and disc space spreader. The nerve root retractor has a tubular body. The tubular body has an inside diameter, a proximal end, a distal end, and a tang extending from the distal end formed to enter the intradiscal space between vertebral bodies in a position to protect and retract a nerve root and to contact adjacent vertebral bodies and maintain a disc space therebetween. The bone chisel has a chisel body for extension through the tubular body inside diameter, the chisel body further having a proximal end and a distal end. The chisel body is configured for passage through the tubular body inside diameter and for extension of the proximal and distal ends thereof from the tubular body proximal and distal ends, respectively, so that the chisel distal end is disposed adjacent the tang for bone cutting operations. Cutting means is situated on the chisel body distal end. The cutting means has a curvature substantially in conformance with the curvature of the tubular body inside diameter. Means is situated on the chisel body proximal end for manipulating the cutting edge. Chisel and guide apparatus is disclosed for removal of bone from adjacent vertebral bodies during performance of laminectomy procedures. A tubular body has an inside diameter, a proximal end and a distal end. A tang extends from the distal end, the tang having a length and width for contacting adjacent vertebral bodies and for entering the vertebral body intradiscal space to maintain a predetermined space therebetween. A chisel body is formed to extend through the tubular body inside diameter, having a proximal end and a distal end. The chisel body proximal end extends from the tubular body proximal end for longitudinal and rotational manipulation. The chisel body is formed for maneuverability of the chisel body distal end adjacent the tang. Cutting means is provided on the chisel body distal end.

Further, apparatus is disclosed for removal of bone from selected portions of adjacent vertebral bodies having a vertebral disc space therebetween during laminectomy procedures. A tubular body has a proximal end and a distal end and also has an inside diameter. Tang means is attached to the tubular body distal end. The tang means has a width for contacting and spacing the adjacent vertebral bodies and has a length for entering the vertebral disc space. Chisel means has a chisel body for extending through the tubular body with a distal end extending from the tubular body distal end to a position adjacent the tang means. The chisel means further has a proximal end extending from the tubular body proximal end. Means is provided for manipulation of the chisel means that is mounted on the chisel means proximal end. Cutting means is provided on the chisel means distal end.

BRIEF DESCRIPTION OF THE DRAWINGS

FIG. 1 is an elevation of the nerve root retractor and disc space spreader used in conjunction with the present invention.

FIG. 2 is a perspective of the nerve root retractor and disc space spreader used in conjunction with the present invention.

FIG. 3 is an elevation of one embodiment of the present invention.

FIG. 4 is an elevation of another embodiment of the present invention.

FIG. 5 is an elevation of an additional embodiment of the present invention.

FIG. 6 is a section along the line 6—6 of FIG. 5.

DESCRIPTION OF THE PREFERRED EMBODIMENTS

The embodiments of the bone removal chisel described herein are used in conjunction with the nerve root retractor and disc space spreader. The disclosed invention is useful in procedures involving placement of materials and devices such as the RAY Threaded Fusion Cage (™).

With reference now to FIG. 1, a nerve root retractor and disc space spreader 23 described and claimed in the aforesaid patent application, Attorney's Docket No. A0081, is shown. An impact portion 24 is shown at a proximal end of the nerve root retractor 23. The retractor has a tubular body 26 with a single tang 27 extending from a distal end of the tubular body 26. It should be understood that the tubular body may have openings in the walls thereof extending along portions of or the entire length of the body. The tang or projection 27 is configured to be interposed within the intradiscal space between vertebral bodies and is joined to the end of the tubular body 26 at a shoulder 28. A cut-away portion 29 is shown at the distal end of the tubular body 26 extending from the shoulder 28 toward the proximal end of the nerve root retractor 23. The arrangement of the configuration of the nerve root retractor is further seen in perspective in FIG. 2. The extending tang 27 is seen to be joined to the distal end of the tubular body 26 by the shoulder 28, one of which is situated on either side thereof. The distal end of the nerve root retractor body 26 is therefore seen to be that extent of the body 26 which reaches a position adjacent the shoulders 28 and from which the single tang 27 extends. The cut-away portion 29 in the wall of the tubular body 26 is seen to be made in that side of the tubular body which is opposed to the side from which the tang 27 extends. In addition, a window 31 is shown in solid line in FIG. 2 through which a surgeon's assistant may view the operating area within and around the distal end of the tubular body for purposes of applying suction, etc., during the operating procedure. Meanwhile, the surgeon may view the operating area through the cut-away portion 29 of the tubular body 26 which is also in proximity with the operating area.

While the nerve root retractor is preferred for use with the bone chisel invention embodiments disclosed herein, these chisel inventions are useful as well with similar instruments including the double tang retractor used for placement of the Ray Threaded Fusion Cage (™). The double tang retractor and the single tang retractor are available in a variety of sizes to accommodate patient anatomical differences. Typical nerve root retractor inside diameters are, for example, 12 millimeters, 14 millimeters, 16 millimeters and 18 millimeters. The dimensions of the chisels of the present invention to be hereinafter described are also varied to correspond to the inside diameter of the nerve root retractor used in the operating procedure, and to have sufficient length so that their proximal and distal ends extend beyond the proximal and distal ends respectively of the nerve root retractor used in the procedure.

With reference to FIG. 3 of the drawings, a bone chisel of the present invention for use in laminectomy procedures is shown having a chisel body 32 with an outside diameter corresponding to the inside diameter of the size-specific nerve root retractor 23 selected for use in the procedure. The chisel body has a serrated cutting edge 33 at the distal end thereof and a T-shaped handle 34 attached to the chisel body 32 by a handle extension 36 at the proximal end thereof. The bone chisel of FIG. 3 is therefore configured for sliding action both longitudinally and rotationally within the inside diameter of the nerve root retractor 23 so that when the serrated cutting edge 33 is moved longitudinally within the retractor to be placed against a portion of bone, rotation of the chisel body 32 by rotating the T-handle 34 produces a cutting action at the bone by the serrated cutting edge 33.

With reference now to FIG. 4 of the drawings, an additional embodiment of the bone chisel of the present invention is shown. A chisel body 37 has a diameter configured for sliding movement between the outside surface of the chisel body 37 and the inside diameter of the nerve root retractor 23. The distal end of the chisel body 37 has a sharp cutting edge 38, wherein the cutting edge lies within a single plane. An impact cap 39 is attached to the proximal end of the bone chisel of FIG. 4. When the cutting edge 38 is placed against a portion of bone to be removed and the impact cap 39 is tapped with a mallet (not shown), cutting edge 38 serves to smoothly cut through the contacted bone portion for removal.

In FIG. 5 of the drawings, an additional embodiment of the present invention is shown, wherein the bone chisel has a chisel body 41 with an impact cap 42 attached to the proximal end thereof. The chisel body 41 is shown as a longitudinal section having an outside dimension which is somewhat smaller than the inside diameter of the nerve root retractor 23. A cutting edge attachment member 43 is shown attached to the distal end of the chisel body 41. The cutting edge attachment member 43 has a free end to which is attached a cutting blade 44 having a cutting edge 46 which lies substantially in one plane. The outside diameter of the cutting blade 44 is configured to pass through in sliding relationship with the inside diameter of the size-specific nerve root retractor 23. The outside diameter of the chisel body 41 of FIG. 5 being lesser than the inside diameter of the size-specific nerve root retractor 23, the longitudinal axis of the bone chisel of FIG. 5 may be caused to depart from the longitudinal axis of the nerve root retractor to thereby provide for making bone cuts at an angle to the longitudinal axis of the nerve root retractor. Cutting is accomplished at the cutting edge 46 by tapping on the impact cap 42 with a mallet (not shown). The configuration at the distal end of the chisel body 41 is shown in FIG. 6, wherein the cutting edge 46 is positioned at the free end of cutting blade 44 which is attached to the chisel body 41 by the attachment member 43. It may be seen in FIG. 6 that the cutting blade 44 occupies an arc of a circle.

The lengths of the chisels shown in the embodiments of FIG. 3, FIG. 4 and FIG. 5 are sufficient for the distal end of the bone chisels carrying the cutting edges 33, 38 and 46 to extend beyond the distal end of the nerve root retractor 23 to contact selected bone segments and for the proximal end of the chisels to extend outwardly beyond the proximal end of the nerve root retractor 23 so that the proximal ends of the bone chisels at the T-handle 34 and impact caps 39 and 42 are available to a surgeon for manipulation of the cutting edges.

Although the best mode contemplated for carrying out the present invention has been shown and described herein, it will be understood that modification and variation may be made without departing from what is regarded to be the subject matter of the invention.

What is claimed:

1. A bone chisel and guide for use in laminectomy procedures, comprising a nerve root retractor and disc space spreader having a tubular body, said tubular body having an inside diameter, a proximal end, a distal end, and a tang extending from said distal end having a length and width for entering an intradiscal space between vertebral bodies and for contacting adjacent vertebral bodies and maintaining a disc space therebetween, a chisel body having a length extending through said tubular body inside diameter and having a proximal end and a distal end, said chisel body being configured for passage through said tubular body inside diameter and for extension of said proximal and distal ends from said tubular body proximal and distal ends respectively, said chisel body length providing extension of said chisel body distal end to positions adjacent said tang, cutting means on said chisel body distal end, said cutting means having a curvature substantially in conformance with the curvature of said tubular body inside diameter, and means on said chisel body proximal end for manipulating said cutting edge.

2. The bone chisel and guide of claim 1 wherein said chisel body comprises a longitudinal section having outside dimensions substantially smaller than the tubular body inside diameter, whereby the tubular body and said longitudinal section are formed to depart from coaxial relationship for maneuvering said cutting means.

3. The bone chisel and guide of claim 2 wherein said cutting means comprises a cutting blade extending from said chisel body distal end, said cutting blade having a cutting edge lying substantially in one plane and a blade curvature substantially fitting within the tubular body inside diameter.

4. The bone chisel and guide of claim 1 wherein said means for manipulating said cutting edge comprises an impact cap.

5. The bone chisel and guide of claim 1 wherein said chisel body comprises a longitudinal member having an outside dimension for sliding contact with the tubular body inside diameter, whereby the tubular body and said longitudinal member are held in a substantially coaxial relationship.

6. The bone chisel and guide of claim 5 wherein said cutting means comprises a curved serrated cutting edge on said chisel body distal end.

7. The bone chisel and guide of claim 6 wherein said means for manipulating comprises a T-shaped handle for imparting rotational motion to said curved serrated cutting edge.

8. The bone chisel and guide of claim 5 wherein said cutting means comprises a curved cutting edge lying substantially in one plane on said longitudinal member distal end.

9. The bone chisel and guide of claim 8 wherein said means for manipulating comprises an impact cap.

10. Chisel and guide apparatus for removal of bone from ones of adjacent vertebral bodies during laminectomy procedures, comprising a tubular body having an inside diameter, a proximal end and a distal end, a tang extending from said distal end, said tang having a length and width for contacting adjacent vertebral bodies and for entering vertebral body intradiscal space to maintain a predetermined space therebetween, a chisel body formed to extend through said tubular body inside diameter and having a proximal end and a distal end, said chisel body proximal end extending from said tubular body proximal end for longitudinal and rotational manipulation, said chisel body being formed for maneuverability of said chisel body distal end adjacent said tang, and cutting means on said chisel body distal end.

11. Apparatus as in claim 10, comprising means on said chisel body proximal end for manipulating said cutting means longitudinally and rotationally.

12. Apparatus as in claim 10 wherein said chisel body has an outside diameter providing a substantially sliding fit with said tubular body inside diameter.

13. Apparatus as in claim 10; wherein said cutting means comprises a serrated cutting edge.

14. Apparatus for removal of bone from selected portions of adjacent vertabral bodies during lamenectomy procedures wherein the vertebral bodies have a vertabral disc space therebetween, comprising a tubular body having a proximal end and a distal end and having an inside diameter, tang means attached to said tubular body distal end, said tang means having a width for contacting and spacing the adjacent vertebral bodies and for entering the vertabral disc space, chisel means having a chisel body for extending through said tubular body with a distal end extending from said tubular body distal end to positions adjacent said tang means, said chisel means further having a proximal end extending from said tubular body proximal end, means for manipulating said chisel means mounted on said chisel means proximal end, and cutting means on said chisel means distal end.

15. The apparatus of claim 14, comprising an outside diameter on said chisel body that provides a substantially sliding fit with said tubular body inside diameter.

16. The apparatus of claim 14, wherein said cutting means comprises a serrated edge.

* * * * *